United States Patent [19]

Holtkamp, Sr.

[11] Plant 4,577

[45] Jul. 22, 1980

[54] AFRICAN VIOLET PLANT

[76] Inventor: Hermann Holtkamp, Sr., Kueningsmuehle, 2 Dingden, 4236 Hamminkeln, Fed. Rep. of Germany

[21] Appl. No.: 23,473

[22] Filed: Mar. 23, 1979

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet plant having vigorous and compact growth habit; intensive blue-violet flowers carried on 7-9 flower stems, with up to 12 or more flowers per stem; attractive dark green, shiny leaves, and by its long lasting and non-dropping flowers.

1 Drawing Figure

The present invention comprises a new and distinct cultivar of African violet plant, botanically known as *Saintpaulia ionantha,* and hereinafter referred to by the cultivar name Michelle. The new cultivar was referred to during the breeding and selection process by the designation XXI/16-3/79, and is a product of a planned breeding program. The new cultivar is generally characterized by a rich abundance of blue-violet flowers carried by strong upright stems well above the leaves. There are 7-9 flower stems at full flowering, each carrying 7-12 single flowers, thereby providing a full and right bouquet. These traits in combination were not present in previously available commercial cultivars.

The new cultivar was originated from a cross made in a controlled breeding program in Isselburg, Rhineland, Germany. The female, or seed parent was a cultivar designated 26 AN/Z blue-violet, single, an unpatented variety. The male or pollen parent was a cultivar designated B 229/11 pink single, also unpatented.

The new cultivar Michelle was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of the new cultivar, Michelle, which in combination distinguish this African violet as a new and distinct cultivar:

(1) Vigorous growth habit.

(2) Attractive dark green, shiny leaves.

(3) 7-9 flower stems, strong and upright, with 12 or more single flowers on short peduncles.

(4Intensive violet-purple flower color.

(5) Flowers do not fade when maturing, and do not drop.

(6) Very long lasting flowers.

(7) Compact growth habit.

The accompanying photographic drawing shows a typical specimen plant of the new cultivar. The colors appearing in the photograph are as true as possible with color illustrations of this type.

In the following description, color references are made both to the Royal Horticultural Society color chart (RHS) and the Horticultural Color CHART (HCC) issued by Wilson Colour Ltd., except where general color terms of ordinary significance are obvious.

Botanical classification: *Saintpaulia ionantha,* Ramat. cv Michelle.

Parentage:

*Male parent.*—B229/11 pink single.

*Female parent.*—26 AN/Z blue-violet single.

Propagation: The new cultivar holds its distinguishing characteristics through successive propagations by leaf cuttings and by division of shoots.

Plant: From 8 cm. to 10 cm. tall when grown in pots, and approximately 25 cm. in diameter when fully grown.

*Leaves.*

*General form.*—Round to heart shaped.

*Diameter.*—55-60 mm.

*Texture.*—Soft.

*Aspect.*—Velvety, hairy, smooth edges.

*Veins.*—Underside well pronounced, color HCC maroon 1030/1; veins are slightly hairy.

*Color (upperside).*—RHS yellow-green 147A.

*Color (underside).*—HCC maroon 1030/1.

*Petiole.*—Round, strong, hairy, brown-reddish.

Flowers:

*Buds.*—Ball-shaped, 6-7 mm. before opening.

*Sepals.*—5 in number. Color: dark brown, HCC maroon 1030/1. Calyx: flat funnel. Aspect: spear-shaped, hairy. Peduncle: reddish brown, hairy, upright.

Individual flowers:

*Size.*—40-50 mm., flat.

*Color.*—Upperside: HCC violet purple 733. Underside: HCC amethyst violet 35/1.

*Borne.*—Two (2) small and three (3) large petals, upperside very uniform in color, reverse side of petals have flat grooves which run symetrically from the outside towards the center.

*Corolla.*—Violet shaped, smooth edges.

*Arrangement.*—Flowers are on strong, upright stems.

*Flowering time.*—7 weeks after potting first flowers appear; 8-10 weeks to a full bouquet.

Reproductive organs:

*Stamens.*—2 in number.

*Anthers.*—4 anther cells, color RHS yellow-orange 19B.

*Arrangement.*—Two bent or curved short stems, brownish in color, carry the four anther cells.

*Styles.*—Hairy, 7–8 mm. long, base on seed bud is light green.

*Pollen color.*—RHS yellow-orange 19C.

Roots: Very well developed and fine roots, velvety; white when young and active, turning brownish when older.

Disease resistance: No disease problems noticed to date.

General observations: The rich abundance of violet-purple flowers carried centrally on strong stems provides a tight flower bouquet above the leaves. The growth habit is vigorous and compact.

I claim:

1. A new and distinct cultivar of African violet plant as shown and described, characterized by the combined features of vigorous and compact growth habit; intensive blue-violet flowers carried on 7–9 flower stems, with up to 12 or more flowers per stem; attractive dark green, shiny leaves, and by its long lasting and non-dropping flowers.

* * * * *

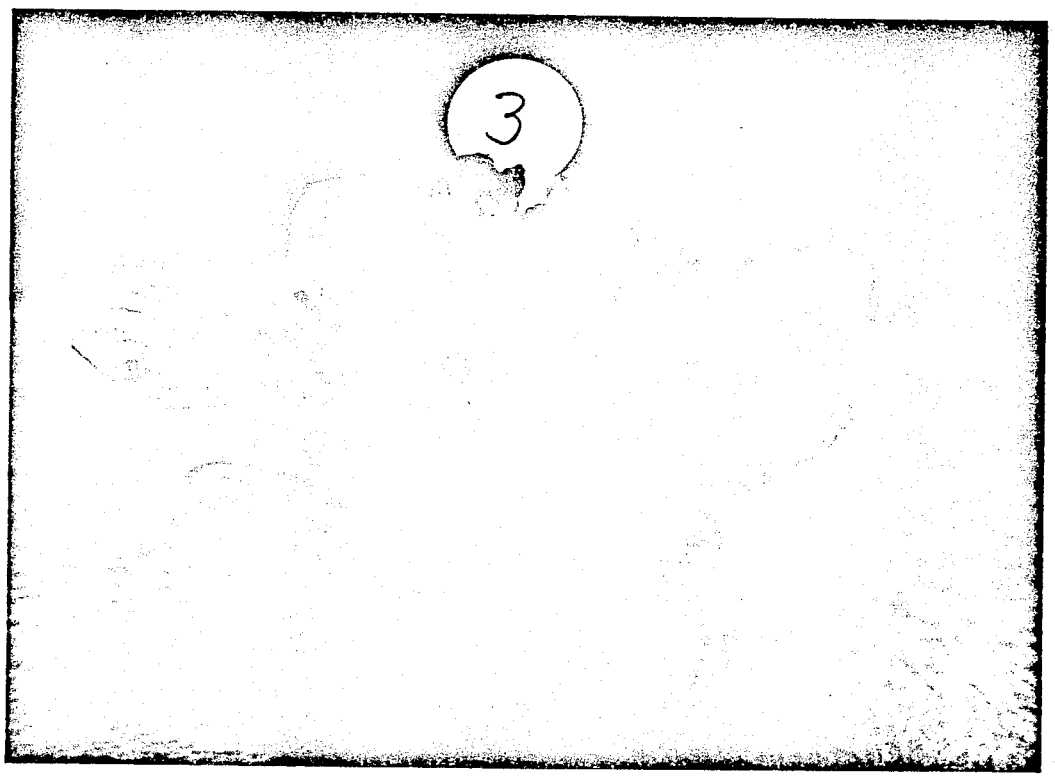
3